United States Patent
Kadesky

(10) Patent No.: US 12,090,293 B2
(45) Date of Patent: Sep. 17, 2024

(54) BURN AND WOUND HEALING SUIT AND METHOD

(71) Applicant: Yale Mitchell Kadesky, Escondido, CA (US)

(72) Inventor: Yale Mitchell Kadesky, Escondido, CA (US)

(*) Notice: Subject to any disclaimer, the term of this patent is extended or adjusted under 35 U.S.C. 154(b) by 0 days.

(21) Appl. No.: 18/048,841

(22) Filed: Oct. 22, 2022

(65) Prior Publication Data
US 2023/0321418 A1    Oct. 12, 2023

Related U.S. Application Data

(60) Provisional application No. 63/362,559, filed on Apr. 6, 2022.

(51) Int. Cl.
*A61M 35/00*    (2006.01)
*A41D 13/12*    (2006.01)
*A61F 5/451*    (2006.01)

(52) U.S. Cl.
CPC ......... *A61M 35/10* (2019.05); *A41D 13/1263* (2013.01); *A61F 5/451* (2013.01); *A61M 2205/3653* (2013.01); *A61M 2205/7545* (2013.01)

(58) Field of Classification Search
CPC ........... A41D 13/1263; A61F 13/00062; A61F 13/146; A61F 2013/00157; A61F 2013/00217; A61F 2013/00536; A61F 5/451; A61G 7/0005; A61H 2033/0004; A61H 2033/0037; A61H 33/00; A61M 1/917; A61M 1/92; A61M 2205/3653; A61M 2205/7545; A61M 2210/083; A61M 2210/086; A61M 35/00; A61M 35/10; B64G 6/00
See application file for complete search history.

(56) References Cited

U.S. PATENT DOCUMENTS

| | | | | |
|---|---|---|---|---|
| 2,749,558 | A * | 6/1956 | Constantin | A61F 5/451 4/316 |
| 4,353,359 | A * | 10/1982 | Milbauer | A61G 10/005 607/108 |
| 4,375,812 | A * | 3/1983 | Vaseen | A61H 33/00 128/202.25 |
| 5,383,918 | A * | 1/1995 | Panetta | A61F 7/0053 607/104 |
| 6,927,316 | B1 * | 8/2005 | Faries, Jr. | A61F 15/006 602/14 |
| 2005/0203452 | A1 * | 9/2005 | Weston | A61M 1/915 602/13 |

* cited by examiner

*Primary Examiner* — Leslie A Lopez
*Assistant Examiner* — Jihad Dakkak
(74) *Attorney, Agent, or Firm* — Law Office of Scott C Harris

(57) ABSTRACT

A burn/wound healing suit with circulating healing anesthetizing and antiseptic liquid. The healing suit is formed of modular parts, including a torso part, upper extremity parts, and lower extremity parts. Each modular part tapers at an end where it connects to another modular part, or seals at this end to be used individually. A connection part is a rigid tube that goes between the connecting parts to enable fluid connection between the different parts. The fluid is circulated by a pump, and heated and filtered to maintain a sterile environment.

11 Claims, 5 Drawing Sheets

BURN AND WOUND HEALING SUIT AND METHOD

This application claims priority from application No. 63/362,559, filed Apr. 6, 2022, the entire contents of which are herewith incorporated by reference.

BACKGROUND

A conventional treatment of wounds, such as burns, takes the burn/wound patient, twice a day, to a wash station. At the wash station, the patient's dressings are removed, and then the burn/wounds are scrubbed with scrub brushes and antibacterial soap. After the burns/wounds are cleaned and dried, the wounds are then covered with silver sulfadiazine, also called "burn cream", and then are re-dressed.

Treatment of these wounds in this way can be extremely painful to the patients, and can be very difficult for the medical staff who need to carry this out. The scrubbing, and antibacterial materials that are used, may reduce bacterial counts, but also may inhibit the healing, because the antibacterial concoctions which are used have typically been shown to inhibit wound healing.

Burns/wounds which are particularly difficult to heal often result in skin grafting, which is a painful process that leaves significant scarring at the donor and recipient site.

SUMMARY OF THE INVENTION

The inventor recognized that there are a number of drawbacks with the current systems and has conceived of and describes herein, an improved design for care of burns/wounds.

This inventor, during his one-year burn fellowship, observed beneath the burned tissue a living, healthy layer of deep skin (dermis) and/or superficial subcutaneous tissue with hair follicles. He observed this in eighty percent of excised and grafted burn patients. These deep layers are capable of regenerating a new skin or epidermis, avoiding excision and grafting. This invention is designed to provide these deep layers with an optimal medium for growing a new epidermis, akin to cultured skin cells grown on an optimal culture medium.

The present application describes a liquid tight suit that can cover a patient's extremities and torso but not the face. The suit is modular in that different parts of the suit can be connected together or used individually. The suit is used as described herein to circulate a fluid that can assist to heal the wounds, and relieve pain and prevent infection.

DETAILED DESCRIPTION

The present application describes a burn/wound healing suit, as described herein. For purposes of this embodiment, the suit is described as a burn/wound healing suit, intended to address wounds. However, it should be understood, and it is contemplated within the present application, that this system can and does also operate to assist with other kinds of wounds other than burn wounds.

Specific structure used as described herein, however is intended to cover not only the specific embodiments described herein, but the general concept of the invention, including all predictable modifications of these embodiments.

The present application describes a suit, referred to herein as a burn/wound healing suit, which can be used to cover one or more sections of a burn/wound patient's body, and to circulate the healing fluid to sections of the body. In embodiments, the healing fluid can include aloe vera, or other non-caustic healing fluids, topical anesthetics, stem cells and non-toxic antiseptics.

Figure 1:
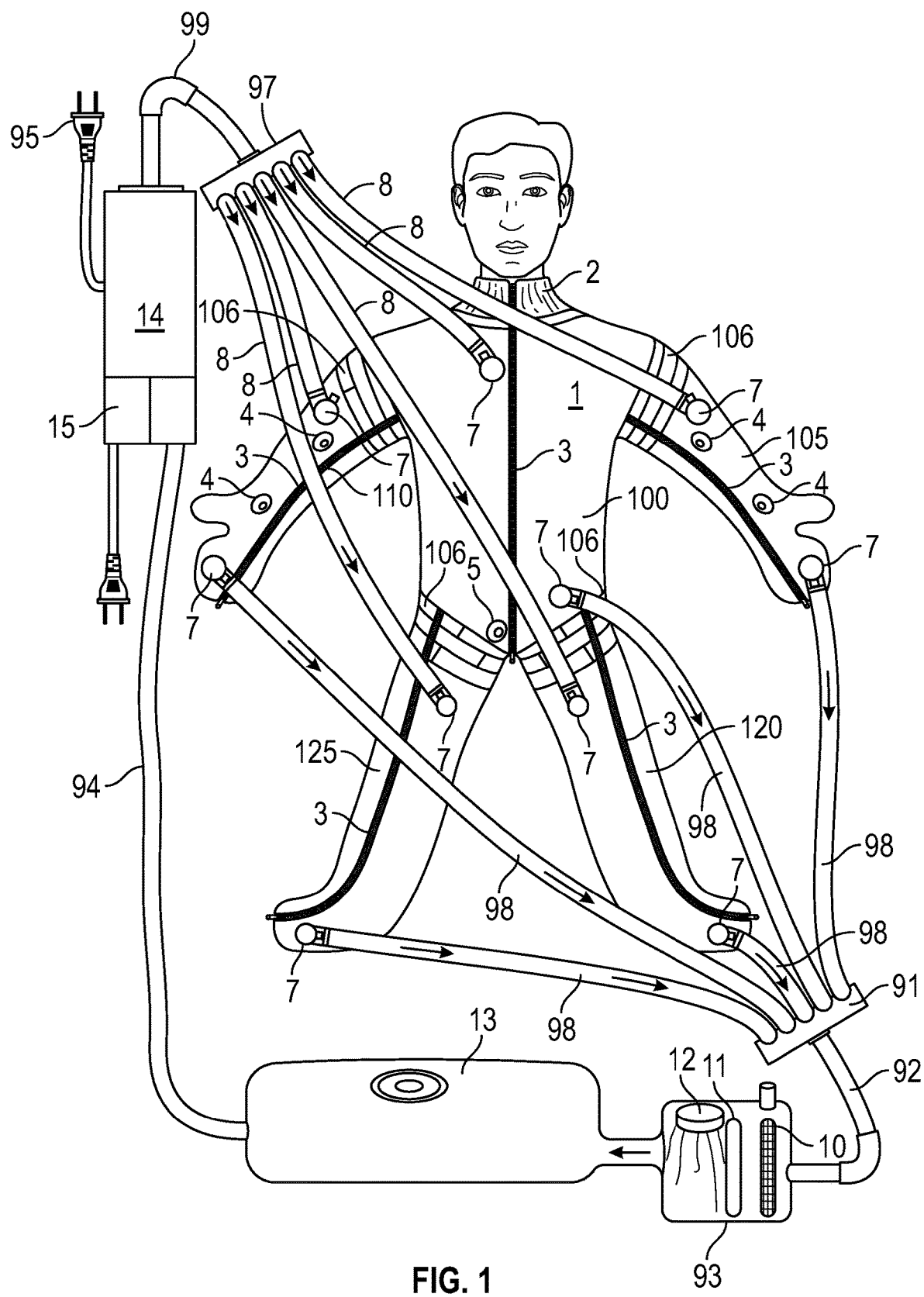
FIG. 1 shows an overall diagram of the suit including the different modular parts connected together.

FIG. 1 shows an overview of the suit. The suit covers all or part of a patient's body that is to receive the healing fluid. The suit 1 can be a neoprene or other suitable material of a thickness and material that has some flexibility, but holds its shape to maintain a space between the suit and the patient. The suit can be made in various sizes including small, medium, large, XL, XXL and XXXL. The suit is also sealed in various locations to form cavities to hold the circulating fluid. An elastic rubber seal 2 is formed around the neck to seal at the neck location. The suit opens and closes using a waterproof zipper, 3, such as a Gore-Tex zipper or other waterproof or water-resistant closure. By using such a zipper, the suit can be applied comfortably, and removed and opened so that it can be cleaned.

A waterproof rubber opening 4 can be used to provide a conduit for venous or arterial catheters, which can be maintained in the patient's body for an extended period of time. There are similarly, rubber openings 5 which allow exit of bladder catheter.

The burn/wound suit is formed of multiple different connectable sections. A torso section 100 connects to upper extremity sections 105, 110, and lower extremity sections such as 120. 125. A watertight seal 106, described in further detail herein, seals between the individual sections. The watertight seal 106 can include a rigid adapter, rubber seals on each side, and Velcro fasteners over the seals, as explained with reference to FIGS. 3-5.

These seals hold the different parts of the suit together, to enable the suit to be easily put on and off of a burn/wound patient.

The suit receives the burn/wound healing fluid, also referred to herein as a healing medium, over a tubing assembly shown as 8, received into a quick connect connector 7. The quick connect connector 7 is a watertight connector attached to components of the burn/wound suit, which receives the healing fluid through the tubing 8. The healing fluid can also be returned via return lines 98, each of which are also attached to one of the quick connect connectors 7.

There are a number of lines connected into and out of the suit. Each line is fed off of main supply line 99 and is connected via a one-to-many adapter 97 which is then connected to the supply hoses, 8, each of which are connected to the suit. The return lines 98 connect via the one-to-many connector 91 to the main return line 92. The return line 92 connects to an exhaust fluid processing system. The exhaust fluid processing system includes a removable filter 10 which can extract the sloughed tissue from the patient, a heating element 11, which maintains the temperature of the healing fluid at an ideal temperature for the body, and a ultraviolet sterilizer light 12, which sterilizes the healing medium.

In embodiments, the heater 11 can be a tubular electric heater, or any kind of resistive heating element. The UV sterilizer 12 can be an ultraviolet lamp inside a quartz sleeve with a retaining coupling.

The filtered, heated and sterilized medium is then passed into a medium tank 13 which contains the ingredients that will be circulated through the unit. The tank 13 is connected via a hose system 94, to pump 14 that circulates the healing medium. The pump 14 can be connected via electrical power 95, and can also include a battery backup 15.

The suit 1, is formed of a number of modular parts which connect together. Different units of the modular part are intended for covering different body parts.

Figure 2:
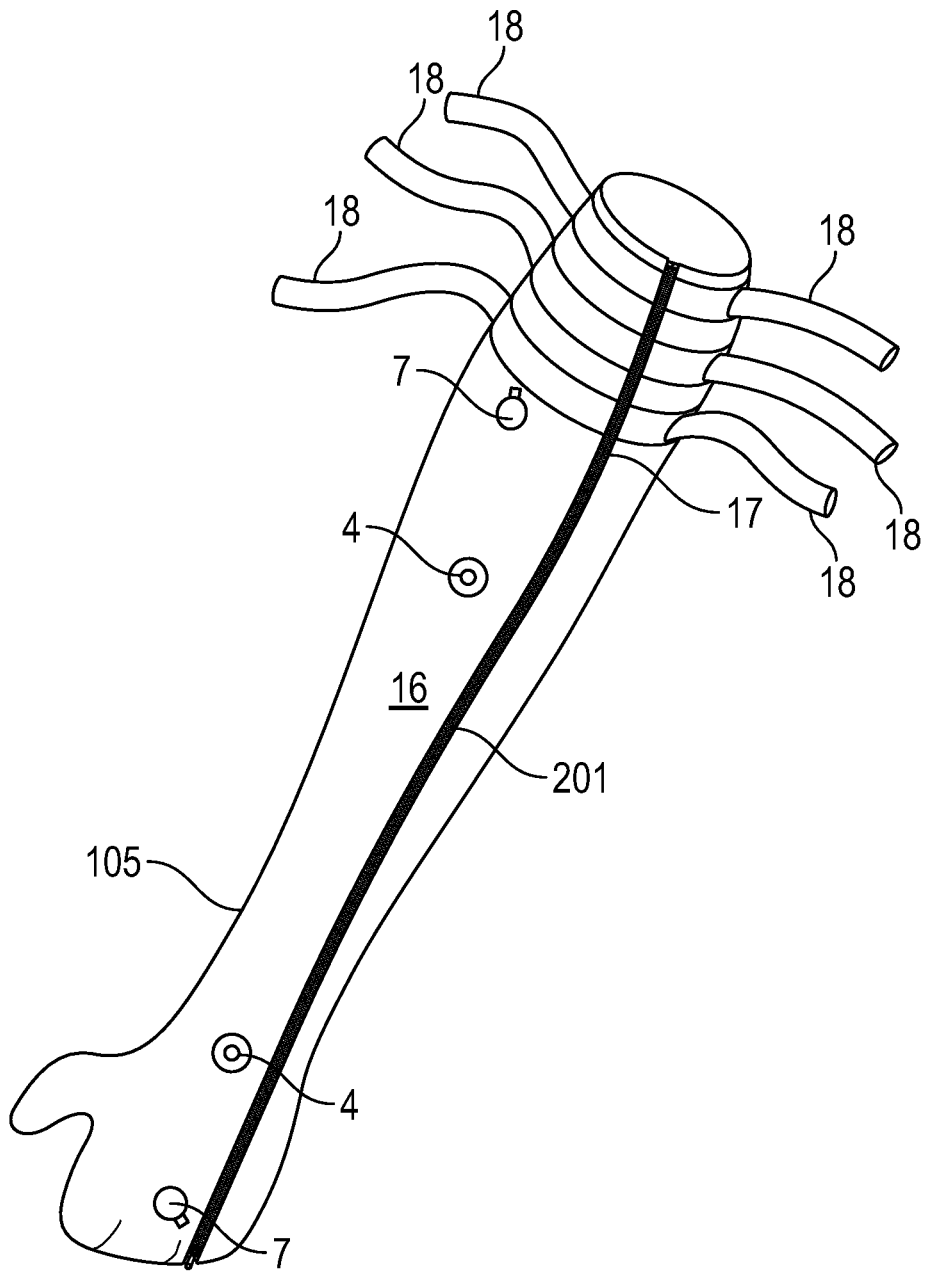
FIG. 2 illustrates a modular part specific for an upper extremity.

FIG. 2 illustrates a right upper extremity unit 105, and there will also be a separate left upper extremity unit. The extremity unit includes a casing 16 which is formed of neoprene, or other suitable material, having a thickness effective to allow the unit to have a certain amount of flexibility, but still maintains some rigidity forming a space between the unit and the patient. The unit also includes a waterproof zipper 201 which allows opening the extremity unit to apply and remove the unit. The extremity unit includes rubber openings, 4, for catheter conduits, and output quick connect connectors for both input and output of fluid. The sleeve is preferably large enough to surround the upper extremity maintaining a space between the unit and the skin. However, in the area 17, the sleeve may taper to fit snugly near the axilla. The sleeve can also connect to the torso unit A number of Velcro straps 18 can be used to enhance the watertight seal in the area secured around the taper area 17.

Figure 3:
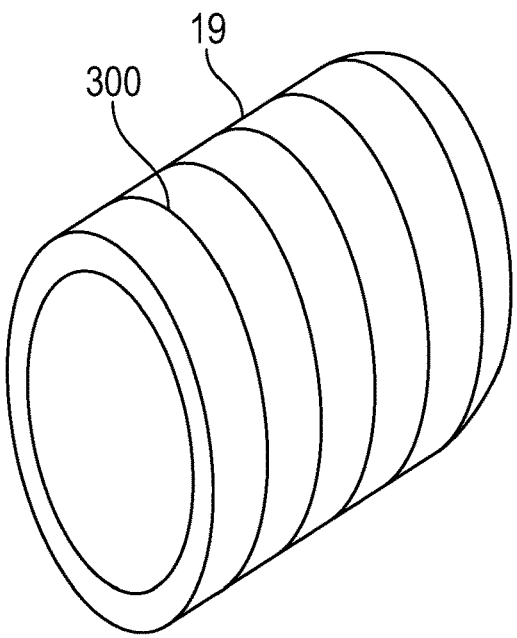
FIG. 3 illustrates a modular connection adapter.
Figure 4:
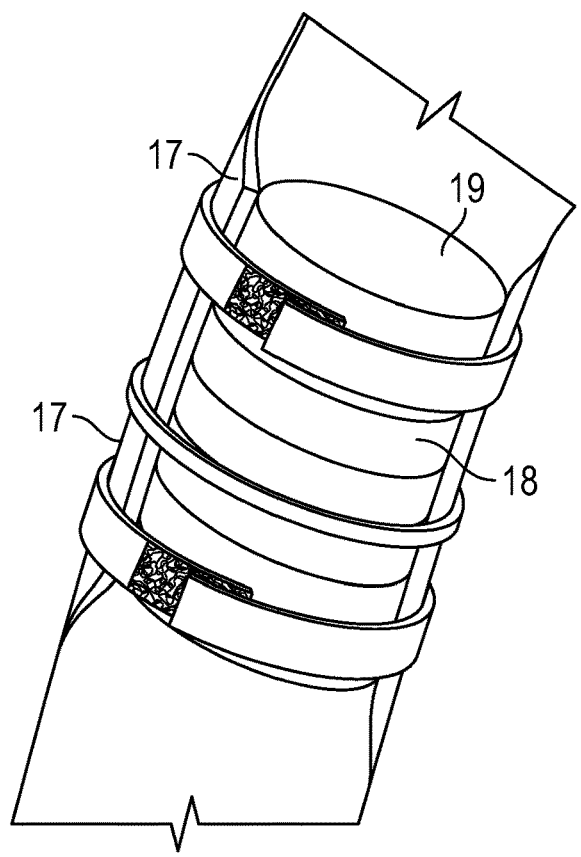
FIG. 4 illustrates how 2 different parts are connected together using the connection adapter.

FIG. 3 illustrates the burn/wound unit connector adapter 19, formed of a cylinder formed with rigid plastic, with supporting ribs 300.

Figure 5:
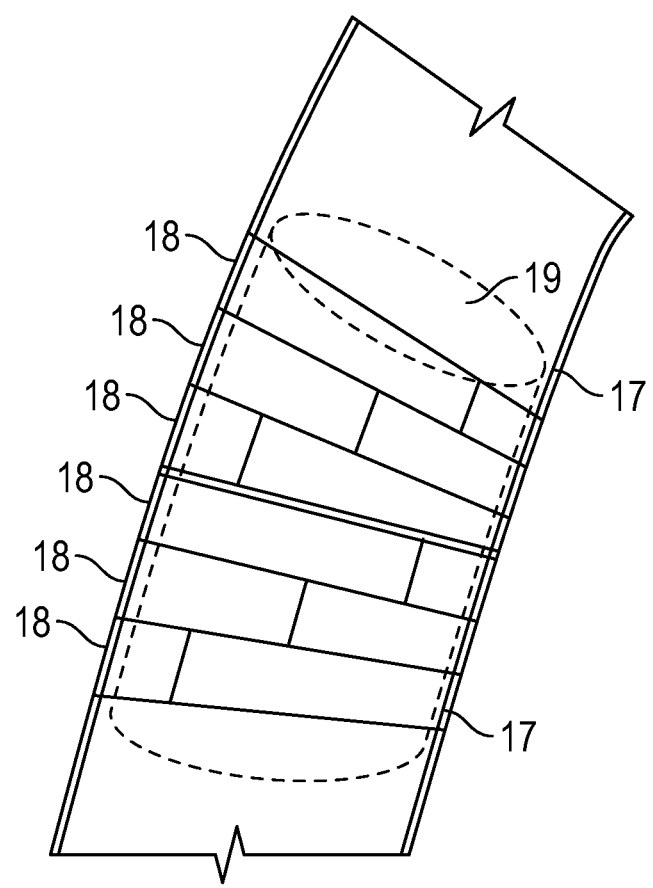
FIG. 5 illustrates how straps are used to hold the modular parts to the connection adapter.

FIG. 5 shows further detail of how these Velcro straps 18 surround and press against the ends of the modular units.

Figure 6:
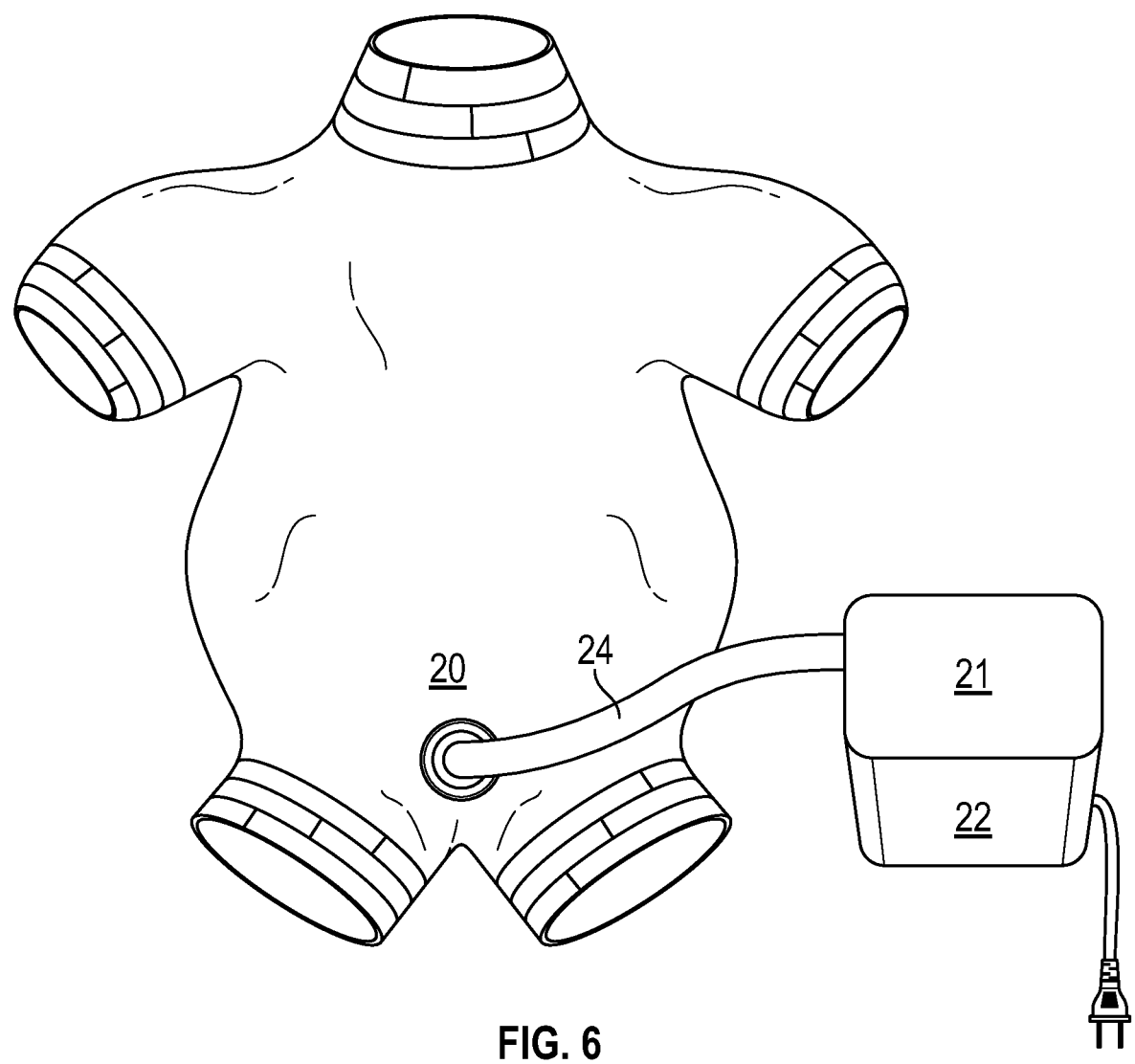
FIG. 6 illustrates a rear view of the torso modular part showing the rectal tube water tight opening.

FIG. 6 illustrates a posterior view of the torso portion of the unit, showing how this posterior view can have a watertight opening 20 in the posterior torso unit near the anus to allow insertion and exit of the rectal tube 24. The rectal tube 24 is itself connected to a feces reservoir 21 and evacuated by a vacuum device 22.

The modular units can include a torso unit as shown in FIG. 1, upper extremity units, and lower extremity units.

In an embodiment, the circulating bath media can include one or more of the medium materials including aloe vera, hyaluronic acid, healing amino acids, vitamins, tropical anesthetics, growth factors, chemical healing stimulants, antiseptics, and stem cells. The intent is for this healing substance to aid in healing, relieve pain and prevent infection, rather than to be a caustic substance as has been conventionally done.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A fluid circulating suit assembly, comprising:
   a suit, having plural different connected parts, including at least a torso covering part and an extremity covering part, the suit formed of a water tight material,
   and the suit having a watertight closure, that is opened to wrap around a body part and is closed to seal around the body part,
   the suit formed of a material that maintains a space between an inside surface of the suit, and the body part in an area of the suit;
   the suit including plural different fluid supply ports, supplying fluid into the space between the inside surface of the suit and the body part, and plural different fluid exhaust ports, removing fluid that has passed in the space between the inside surface of the suit and the body part;
   wherein the extremity covering part is shaped to cover an extremity of a user and where the torso covering part is shaped to cover a torso of the user,
   and where the extremity covering part attaches to the torso covering part,
   where the torso covering part tapers at an end where the torso covering part attaches to the extremity covering part,
   and where the extremity covering part tapers at an e d where the extremity covering part attaches to the torso covering part,
   a connection adapter, formed of a rigid material forming a rigid outer surface,
   the connection adapter fitting inside the suit and where the rigid outer surface being wholly inside the suit and extending between the end of torso covering part where the torso covering part is tapered and the end of the extremity covering part where the extremity covering part is tapered,
   the end of the torso covering part sealing to the outer surface of a first side of the connection adapter;
   the end of the extremity cover part sealing to the outer surface side of the the connection adapter;
   the sealing of the torso covering part and the extremity covering part to the connection adapter forming a watertight seal between the torso covering part and the extremity covering part.

2. The suit assembly as in claim 1, wherein the torso covering part and the extremity covering part each have closure straps that tighten against the outer surface of the connection adapter to enhance the water tight seal between the torso covering part and the extremity covering part and the connection adapter.

3. A suit assembly as in claim 1,
   wherein the rigid outer surface connection adapter is cylindrical.

4. The assembly as in claim 3, wherein the fluid is a bath media that includes one or more medium materials including aloe vera, hyaluronic acid, healing amino acids, vitamins, tropical anesthetic, growth factors, chemical healing stimulants, antiseptics, and stem cells, and where the bath media includes no caustic substances.

5. The assembly as in claim 3, further comprising a pump that circulates the fluid into the fluid supply ports, and receives exhausted fluid from the fluid exhaust ports and where the fluid supply ports are on a first end of each modular portion, and the fluid exhaust ports are on a second end of said each modular portion opposite from the first end of the modular portion.

6. The assembly as in claim 5, further comprising, an exhaust fluid processing system, comprising of a filter that removes particulates from the exhausted fluid, a heater that heats the exhausted fluid to a body temperature, and a sterilizer that sterilizes the exhausted fluid, the exhaust fluid processing system located between the exhaust ports and the pump.

7. The suit assembly as in claim 3, further comprising at least at least one catheter port.

8. The suit assembly as in claim 7, further comprising a water tight rubber opening is for a rectal tube, and further comprising a feces reservoir and a vacuum device evacuating material from the rectal tube into the feces reservoir.

9. The assembly as in claim 3, wherein the connection adapter has cylindrical supporting ribs supporting the rigid outer cylindrical surface of the connection adapter.

10. The suit assembly as in claim 1, wherein the torso covering part having taper end areas at areas of first and second upper extremities, first and second lower extremities, and at a neck area, Where the plural different connected parts also include upper extremity parts, including a first upper extremity part for a first upper extremity having a taper at an end of the first upper extremity where the first upper extremity part connects to the taper area at the first upper extremity on the torso covering part, and a second upper extremity part for a second upper extremity having a taper at an end of the first upper extremity where the second upper extremity part connects to the taper area at the second upper extremity on the torso covering part.

11. The suit assembly as in claim 10, wherein the plural different connected parts fit together and are tightened together relative to one another at areas of the taper.

* * * * *